(12) United States Patent
Ball

(10) Patent No.: US 6,810,877 B2
(45) Date of Patent: Nov. 2, 2004

(54) HIGH SENSITIVITY PRESSURE SWITCH

(75) Inventor: Kenneth H. Ball, Rancho Palos Verdes, CA (US)

(73) Assignee: Medical Electronics Devices Corp., Torrance, CA (US); .

( * ) Notice: Subject to any disclaimer, the term of this patent is extended or adjusted under 35 U.S.C. 154(b) by 260 days.

(21) Appl. No.: 09/921,864

(22) Filed: Aug. 2, 2001

(65) Prior Publication Data

US 2003/0024531 A1 Feb. 6, 2003

(51) Int. Cl.[7] .............................................. A61M 16/00
(52) U.S. Cl. ........................... 128/204.26; 128/204.18; 128/204.21; 128/204.23
(58) Field of Search ....................... 128/204.18, 204.21, 128/204.19, 204.22, 204.32, 204.29, 205.11, 205.12, 205.18, 205.21, 205.24, 203.12, 203.13, 203.14, 203.26, 203.27

(56) References Cited

U.S. PATENT DOCUMENTS

| | | | | |
|---|---|---|---|---|
| 4,050,458 A | * | 9/1977 | Friend ................... 128/204.23 |
| 5,047,007 A | * | 9/1991 | McNichols et al. ........... 604/20 |
| 5,193,393 A | * | 3/1993 | Czarnocki ..................... 73/708 |
| 5,438,980 A | * | 8/1995 | Phillips .................. 128/204.23 |
| 5,630,411 A | * | 5/1997 | Holscher ............... 128/205.24 |
| 5,794,614 A | * | 8/1998 | Gruenke et al. ....... 128/204.21 |
| 5,823,187 A | * | 10/1998 | Estes et al. ............ 128/204.23 |
| 6,305,374 B1 | * | 10/2001 | Zdrojkowski et al. . 128/204.21 |

* cited by examiner

*Primary Examiner*—Glenn K. Dawson
*Assistant Examiner*—Darwin P. Erezo
(74) *Attorney, Agent, or Firm*—Irving Keschner

(57) ABSTRACT

A circuit for use in respiration type apparatus using a piezoresistive transducer and wherein the temperature effects on system stabilization are minimized and system initialization times are reduced. The circuit comprises a differential sensor amplifier response to the output of the piezoresistive transducer, a dc negative feedback circuit connected to the output of the differential amplifier, an initialization circuit for reducing the initialization time of the circuit, a diode clamp and voltage follower for clamping the voltage output and a voltage comparator for tracking the circuit operating point and switching its output state when a sudden voltage change caused by a patient breath is detected.

4 Claims, 2 Drawing Sheets

HIGH SENSITIVITY PRESSURE SWITCH

BACKGROUND OF THE INVENTION

1. Field of the Invention

The present invention provides an improved circuit for use in use respirator type apparatus wherein the operating point of the apparatus is stabilized over large temperature ranges.

2. Description of the Prior Art

Apparatus for supplying oxygen to a patient in response to the patient's breathing cycles have been available in the prior art. In such devices, the breathing cycles are sensed by a capacitive pressure sensor, or transducer, which provides an electrical output signal corresponding to the breathing cycle. An example of such an apparatus is shown in U.S. Pat. No. 4,612,928 to Tiep et al and U.S. Pat. No. 5,134,886 to the inventor of the present invention. Capacitive transducers however are difficult to manufacture and tend to be hand fabricated, increasing the costs associated therewith. In addition, capacitive transducers tend to drift and fail over time.

In order to overcome the disadvantages of capacitive transducers, efforts have been made to use piezoresistive sensors as a replacement since they are readily available, inexpensive and reliable. In this case, a conventional differential amplifier provides a constant DC voltage output in response to a constant pressure input from the transducer. The amplifier typically has a voltage gain of 7000 or greater in order to detect a momentary nasal inspiration pressure of approximately 0.002 psi. However, it is difficult to maintain the stability of the pressure sensor at this high voltage gain over a large temperature range. Although the sensors can be individually temperature compensated through testing, it is not practical for low cost production requirements.

What is desired is to provide an improved circuit for use in respirator type apparatus wherein a piezoresistive transducer is utilized to sense patient breaths and wherein temperature effects on circuit stabilization are minimized.

SUMMARY OF THE INVENTION

The present invention provides a high sensitivity circuit for use in respiration type apparatus using a piezoresistive transducer and wherein the temperature effects on system stabilization are minimized. In addition, means are provided to reduce system initialization times. The apparatus can be designed to regulate the patient intake of oxygen or medicines, such as insulin and respiratory medicines.

The circuit comprises a differential sensor amplifier which responds to the output of the piezoresistive transducer, a dc negative feedback circuit connected to the output of the differential amplifier, means for reducing the initialization time of the circuit, circuit means for clamping the voltage output and a voltage comparator for tracking the circuit operating point and switching its output state when a sudden voltage change caused by a patient breath is detected.

The present invention thus provides a simple, reliable and inexpensive circuit for stabilizing the temperature effects in a respiration type apparatus using a piezoresistive transducer.

DESCRIPTION OF THE DRAWING

For a better understanding of the present invention as well as other objects and further features thereof, reference is made to the following description which is to be read in conjunction with the accompanying drawing wherein.

DESCRIPTION OF THE INVENTION

Figure 1:
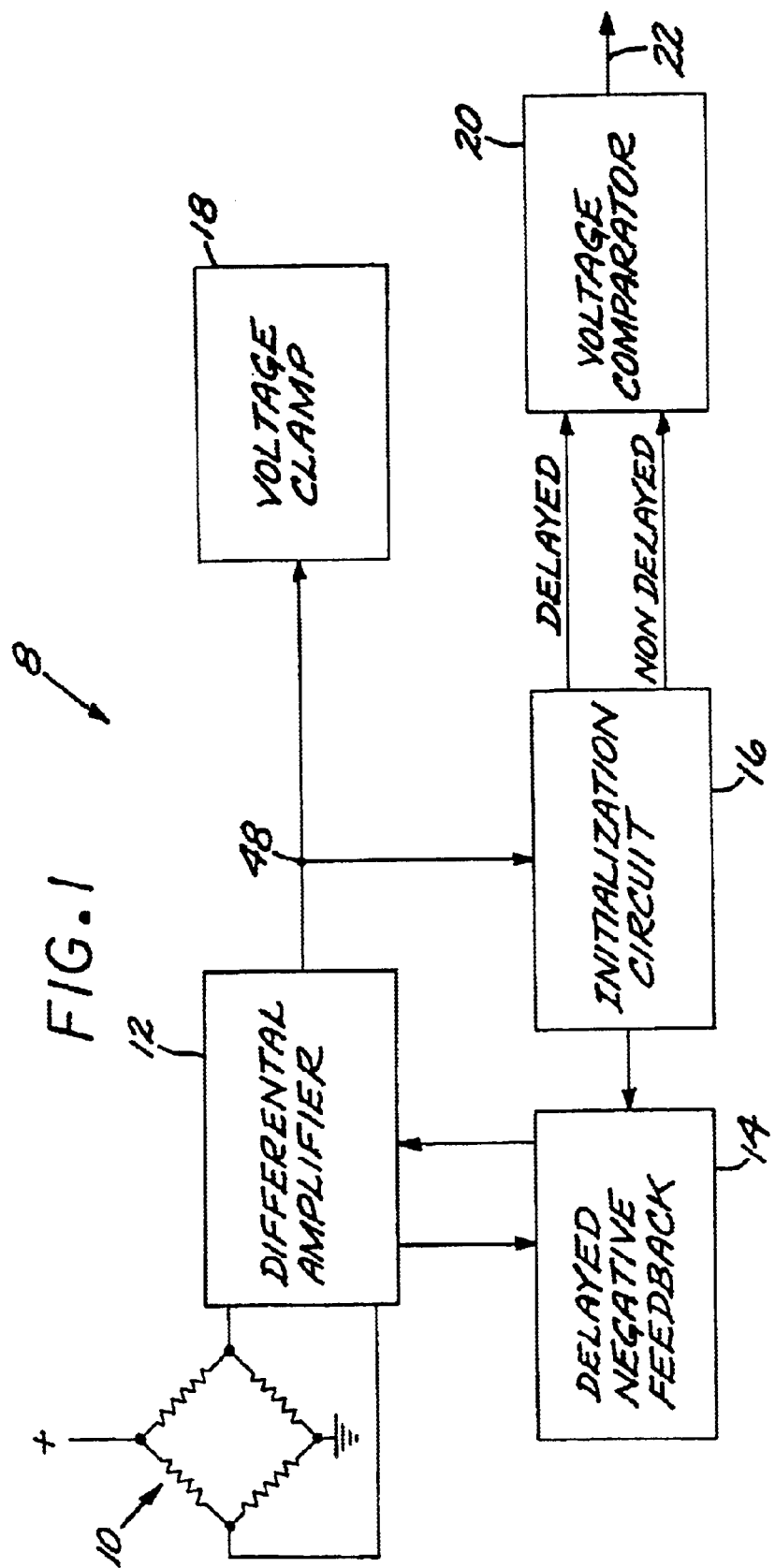
FIG. 1 is a block diagram of the apparatus of the present invention.

Referring now to FIG. 1, a block diagram of the high sensitivity pressure switch circuit 8 of the present invention is illustrated.

The output of a piezoresistive transducer 10 is coupled to differential amplifier 12, the output of which is coupled to a DC negative feedback circuit 14 via initialization circuit 16. Circuit 16 speeds up the initialization process when the system is powered up, enabling the circuit to be balanced and ready to sense breaths relatively rapidly. A voltage clamp 18 is also connected to the output of differential amplifier 12 and prevents large voltage excursions at the detector output due to breath expiration and the pressure released by the respirator apparatus valve allowing the circuit to recover quickly, thus providing the ability of the circuit to sense a number of breaths in a time cycle and to avoid missing or skipping breaths. An operational amplifier 20, used as a voltage comparator, is connected to the output of initialization circuit 16 and tracks the circuit operating point and provides a switching voltage on output lead 22 when a sudden voltage change (breath) occurs. The output of differential amplifier 12 is fed through initialization circuit 16 to delayed negative feedback circuit 14 as illustrated.

Figure 2:
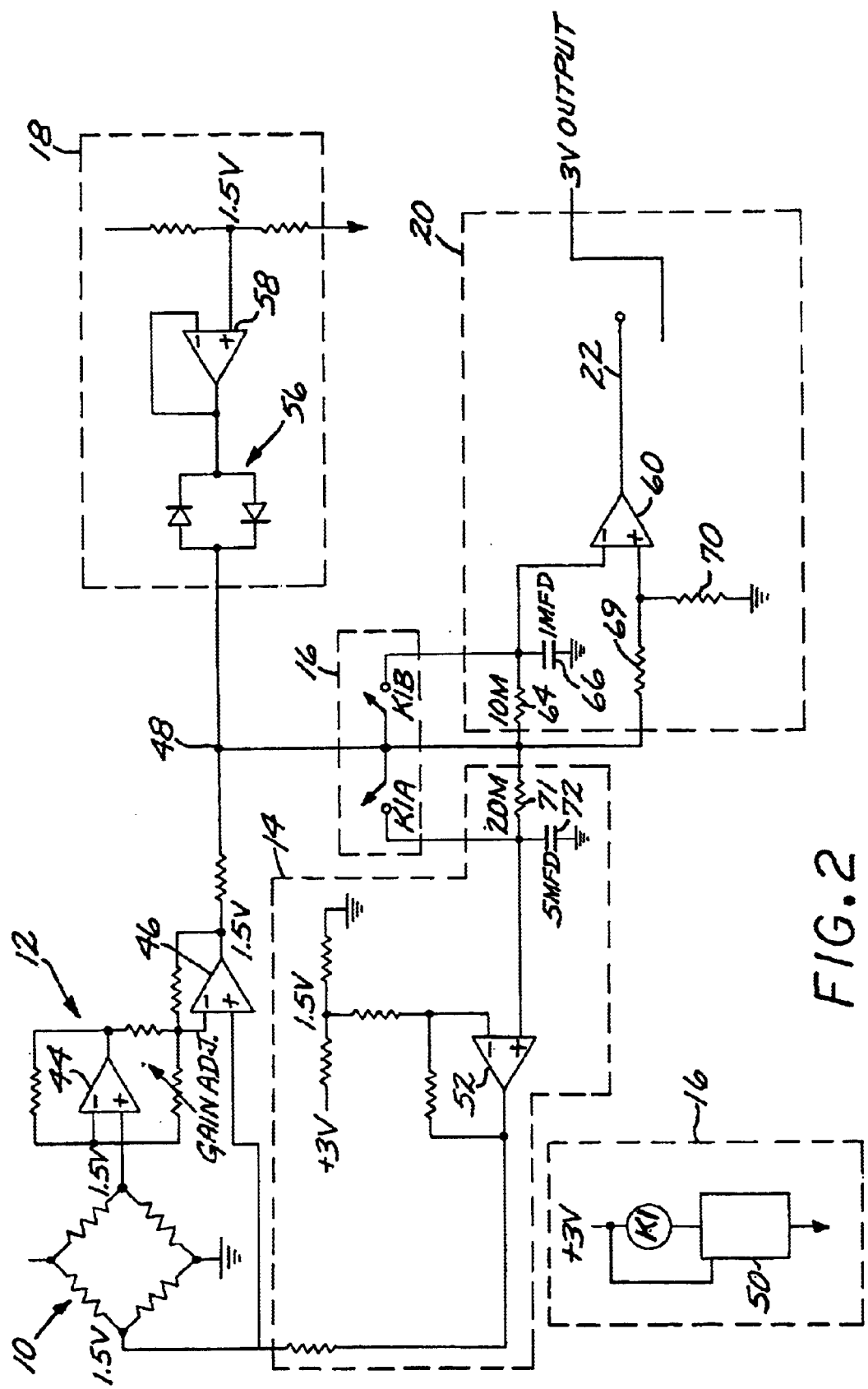
FIG. 2 is a circuit schematic of the block diagram shown in FIG. 1.

FIG. 2 is the schematic diagram for the block diagram shown in FIG. 1.

The output of piezoresistive pressure sensor, or transducer, 10 is applied to the positive input of differential amplifier circuit 12 comprising differential amplifiers 44 and 46, the output voltage at node 48 being designed to be approximately 1.5 volts at system power-up. The voltage output at node 48 is coupled to DC negative feedback circuit 14 via initialization circuit 16 and the delay circuit comprising resistor 71 and capacitor 72.

Circuit 16 comprises momentary relay contacts KIA and KIB (solid state switch can be used) and monostable multivibrator 50, the contacts KIA and KIB being closed when one-shot 50 is triggered—this occurs for approximately one second upon system power up. At this time, initialization circuit 16 shorts out 20 megohm resistor 71 causing capacitor 72 to charge rapidly to the circuit operating point (approximately 1.5 volts). When KIA is closed, the voltage at output node 48 is coupled to the positive input of negative feedback amplifier 52, the output of which is coupled to pressure sensor 10 and one input of differential amplifier 46, resulting in a negative voltage change at node 48. During this one second time period, the overall system gain is essentially zero When KIA opens after the one second time period, the voltages in the circuit are balanced at the proper levels, in this case 1.5 volts. However, a long delay in the feedback is in effect and the AC gain is maximum. Since temperature drift occurs over periods of minutes, DC compensation is fast enough to take place. Gain at very low frequencies (breath rates) is very high; the result is essentially a zero gain at DC (1.5 volts) but a large AC gain at 1 hz and above (1.5 volt input increases slightly) due to the delay circuit. The AC gain occurs when a patient takes a breath.

Voltage clamp 18 comprises a diode clamp circuit 56 and voltage follower 58. The voltage clamp prevents large voltage excursions (operating range of the piezoresistive sensor circuit 10 is preferably maintained between 0.8 volts and 2.2 volts) at the sensor output due to breath expiration and 20 p.s.i. to approximately 50 p.s.i. pressure from oxygen (or medicine) released by the apparatus valve. Voltage clamping allows the circuit to recover rapidly so that approximately 20 breaths per minute can be sensed, preventing breaths from being missed or skipped.

Voltage comparator 20 comprises operational amplifier 60, the output on lead 22 being coupled to the apparatus valve control (not shown). The input to the negative terminal of amplifier 60 is not delayed during this one second power on mode; at this time, the input to the positive terminal of amplifier 60 is delayed by resistor 64 and capacitor 66. The delayed input is set to 0.1 volts below the reference (1.5 volts) by a divider comprising resistors 69 and 70. When the patient takes a breath (after the one second delay), a breath signal is detected by piezoresistive transducer 10 and coupled to the positive input of amplifier 60 (the voltage charge at the negative input of amplifier 60 has essentially no effect due to 10 megohm resistor 64). This voltage change is detected and the output on lead 22 changes state because the reference signal at the negative terminal is essentially unchanged due to the delay provided by resistor 64. Amplifier 60 is initialized, as with the sensor amplifier, through relay contacts KIB upon power up. In essence, the voltage at the negative input of amplifier 60 after warm-up is 1.5 volts, the reference voltage. The voltage at the positive input of amplifier 60 is 1.4 volts with no breath being detected. When a breath (inspiration) is detected, the voltage at node 48 is increased to 1.6 volts or greater, this voltage being coupled to the positive input of amplifier 60. At this time (trip point), amplifier 60 generates an output pulse of short duration on lead 22, the leading edge of the output pulse (3 volt amplitude) corresponding to the breath detection signal. This signal is coupled to the valve control causing gas to be dispensed to the pulmonary tract of the patient.

The present invention thus provides a simple, inexpensive and easily implemented improvement to respirator apparatus which minimizes sensor temperature sensitivity and increases system initialization times while providing high sensitivity.

While the invention has been described with reference to its preferred embodiments, it will be understood by those skilled in the art that various changes may be made and equivalents may be substituted for elements thereof without departing from the true spirit and scope of the invention. In addition, many modifications may be made to adapt a particular situation or material to the teachings of the invention without departing from its essential teachings.

What is claimed is:

1. A circuit for use in a respirator type apparatus, said apparatus delivering gas to the pulmonary tract of a patient during inspiration, said circuit having an operating point comprising:

a piezoresistive pressure transducer responsive to the breath of said patient and generating a signal in response thereto;

a differential amplifier having an output and a gain, said differential amplifier being responsive to said signal;

an initialization circuit coupled to the output of said differential amplifier, said initialization circuit having an output, said initialization circuit becoming operative for a predetermined time period when power is applied to said apparatus, said initialization circuit causing said apparatus to be at said operating point at the end of said predetermined period;

a voltage comparator having an output and first and second inputs said first and second inputs being coupled to the output of said differential amplifier; and a delayed negative feedback circuit coupled to the output of said initialization circuit and having an output; the output of said delayed negative feedback circuit being coupled to said differential amplifier.

2. The circuit of claim 1, wherein the voltage at said first input of said voltage comparator is approximately at said operating point, the voltage at said second input of said voltage comparator being less than said operating point.

3. The circuit of claim 2, wherein the voltage at said first input of said voltage comparator and said second input of said voltage comparator increase on patient inspiration.

4. The circuit of claim 3, wherein the voltage increase at said second input of said voltage comparator is greater than the voltage increase at said first input of said voltage comparator, the voltage difference causing the output of said voltage comparator to change state.

\* \* \* \* \*